(12) United States Patent
Alfano et al.

(10) Patent No.: US 6,240,312 B1
(45) Date of Patent: May 29, 2001

(54) REMOTE-CONTROLLABLE, MICRO-SCALE DEVICE FOR USE IN IN VIVO MEDICAL DIAGNOSIS AND/OR TREATMENT

(76) Inventors: Robert R. Alfano; Scott Alfano, both of 3777 Independence Ave., Bronx, NY (US) 10463; Quan-Zhen Wang, 99 La Salle St., 6G, New York, NY (US) 10027; Ping Pei Ho, 24 W. Terrace Rd., Great Neck, NY (US) 11021

( * ) Notice: Subject to any disclaimer, the term of this patent is extended or adjusted under 35 U.S.C. 154(b) by 0 days.

(21) Appl. No.: 09/178,275

(22) Filed: Oct. 23, 1998

Related U.S. Application Data
(60) Provisional application No. 60/062,743, filed on Oct. 23, 1997.

(51) Int. Cl.[7] ........................................ A61B 6/00

(52) U.S. Cl. .............................. 600/476; 128/903; 348/77

(58) Field of Search .................................. 600/407, 473, 600/476, 585; 128/903; 348/65, 77

(56) References Cited

U.S. PATENT DOCUMENTS

| | | | |
|---|---|---|---|
| 4,278,077 | * 7/1981 | Mizumoto | 128/4 |
| 4,844,076 | * 7/1989 | Lesho et al. | 128/631 |
| 5,131,398 | 7/1992 | Alfano et al. | |
| 5,353,807 | * 10/1994 | DeMarco | 128/772 |
| 5,395,366 | * 3/1995 | D'Andrea et al. | 604/890.1 |
| 5,604,531 | * 2/1997 | Iddan et al. | 348/76 |
| 5,610,488 | 3/1997 | Miyazawa | |
| 5,625,458 | 4/1997 | Alfano et al. | |
| 5,681,260 | * 10/1997 | Ueda et al. | 600/114 |
| 5,833,603 | * 11/1998 | Kovacs et al. | 600/317 |
| 5,984,875 | * 11/1999 | Brune | 600/549 |

OTHER PUBLICATIONS

Motamedi et al., "Miniaturized micro–optical scanners," Optical Engineering, 33 (11), 3616–23 (Nov. 1994).

Gonzalez et al., "Packaging Technology for Miniature IVD Instrumentation," Medical Device & Diagnostic Industry, 70–5 (Apr. 1998).

Motamedi et al., "Micro–opto–electro–mechanical devices and on–chip optical processing," Opt. Eng., 36 (5), 1282–97 (May 1997).

* cited by examiner

*Primary Examiner*—Marvin M. Lateef
*Assistant Examiner*—Shawna Shaw
(74) *Attorney, Agent, or Firm*—Kriegsman & Kriegsman (57) ABSTRACT

Remote-controllable, micro-scale, robotic device for use in diagnosing and/or treating abnormalities inside a human body in vivo. The device has a length from 0.1 mm to 10 mm and can be introduced into the body either from natural body openings or by injection into the blood stream. Once inside the body, the device can be guided to different locations in the body by an outside operator using radio controls and computer software. 2-dimensional image information and spectroscopic information (e.g., fluorescence, absorption, elastic scattering, Raman, etc.) gathered by the device inside the body are transmitted by video and radio signals to a computer located externally relative to the body. The transmitted information is processed, analyzed and displayed by the external computer for use by the outside operator. The outside operator can then make a diagnosis and, if applicable, instruct the device to render a treatment on the examined area. Such treatments include the ablation of tissue using lasers or the like and the binding of ruptured tissues together using chemical glue, UV cured epoxy materials or photochemical or photo-ionization techniques using near-infrared light to weld tissue from absorption at water bands.

30 Claims, 12 Drawing Sheets

REMOTE-CONTROLLABLE, MICRO-SCALE DEVICE FOR USE IN IN VIVO MEDICAL DIAGNOSIS AND/OR TREATMENT

CROSS-REFERENCE TO RELATED APPLICATIONS

The present application claims the benefit under 35 U.S.C. 119(e) of U.S. Provisional Patent Application Ser. No. 60/062,743, filed Oct. 23, 1997, the disclosure of which is incorporated herein by reference.

BACKGROUND OF THE INVENTION

The present invention relates generally to the detection and treatment of diseased and/or abnormal biological materials, such as cells and/or tissues, and relates more particularly to the detection and treatment of diseased and/or abnormal biological materials using photonics.

The use of photonics to image biological materials, to detect abnormal and/or diseased states present therein and/or to treat such abnormalities and disease states has become increasingly more prevalent over the last several years. Examples of patents directed to the use of photonics in the foregoing types of applications include the following, all of which are incorporated herein by reference: U.S. Pat. No. 4,930,516, inventors Alfano et al., issued Aug. 4, 1998; U.S. Pat. No. 5,042,494, inventor Alfano, issued Aug. 27, 1991; U.S. Pat. No. 5,369,496, inventors Alfano et al., issued Nov. 29, 1994; U.S. Pat. No. 5,061,075, inventors Alfano et al., issued Oct. 29, 1991; U.S. Pat. No. 5,131,398, inventors Alfano et al., issued Jul. 21, 1992; U.S. Pat. No. 5,348,018, inventors Alfano et al., issued Sep. 20, 1994; U.S. Pat. No. 5,467,767, inventors Alfano et al., issued Nov. 21, 1995; U.S. Pat. No. 5,261,410, inventors Alfano et al., issued Nov. 16, 1993; U.S. Pat. No. 5,293,872, inventors Alfano et al., issued Mar. 15, 1994; U.S. Pat. No. 5,635,402, inventors Alfano et al., issued Jun. 3, 1997; U.S. Pat. No. 5,474,910, inventor Alfano, issued Dec. 12, 1995; U.S. Pat. No. 5,371,368, inventors Alfano et al., issued Dec. 6, 1994; U.S. Pat. No. 5,413,108, inventor Alfano, issued May 9, 1995; U.S. Pat. No. 5,644,429, inventors Alfano et al., issued Jul. 1, 1997; U.S. Pat. No. 5,625,458, inventors Alfano et al., issued Apr. 29, 1997; U.S. Pat. No. 5,710,429, inventors Alfano et al., issued Jan. 20, 1998; U.S. Pat. No. 5,719,399, inventors Alfano et al., issued Feb. 17, 1998; U.S. Pat. No. 5,769,081, inventors Alfano et al., issued Jun. 23, 1998; U.S. Pat. No. 5,799,656, inventors Alfano et al., issued Sep. 1, 1998; and U.S. Pat. No. 5,813,988, inventors Alfano et al., issued Sep. 29, 1998.

One of the primary benefits of the photonic approach to imaging and examining biological materials is that said imaging and examination can be conducted in vivo in a patient with little risk of injury to the patient. This is to be contrasted with certain conventional imaging techniques, such as X-ray imaging, which involves subjecting a patient to potentially harmful X-ray radiation, and with certain conventional examination techniques, such as biopsy and histological evaluation, which cannot be conducted in vivo. Where the organ or tissue to be examined is located internally, the photonic approach to examination typically involves inserting optical fibers, typically disposed within an endoscope or similar device, into the patient's body in proximity to the area to be examined. The area to be examined is irradiated with light transmitted thereto by the optical fibers, and the light from the irradiated area is collected and transmitted by the optical fibers to a spectroscopic device or camera and computer for observation and analysis.

As can readily be appreciated, one of the current limitations on the use of photonics to image, examine and/or treat biological materials located inside a patient is the ability to access the biological materials wished to be examined using optical fibers and/or endoscopes.

SUMMARY OF THE INVENTION

It is an object of the present invention to provide a novel device that is designed to detect and/or treat diseased and/or abnormal biological materials, such as cells and/or tissues, inside a patient's body.

It is another object of the present invention to provide a device that overcomes at least some of the problems described above in connection with the use of optical fibers and/or endoscopes to access internally disposed biological materials.

In accordance with the teachings of the present invention and in furtherance of the aforementioned objects, there is provided a wireless, remote-controllable, micro-scale device adapted for use inside a patient's body, said wireless, remote-controlled, micro-scale device preferably being 0.1 mm to 20 mm in length and comprising (a) a transport capsule; (b) means for moving said transport capsule inside a patient's body; (c) imaging means, on board said transport capsule, for collecting image information on the appearance of the inside of the patient's body; (d) examining means, on board said transport capsule, for collecting information regarding the presence of abnormal biological materials inside the patient's body; and (e) communication means, on board said transport capsule, for transmitting the information collected by said imaging means and said examining means to a location outside the patient's body. As will hereinafter be described, said examining means preferably includes means for measuring the spectrum of photo-excited tissue, and said examining means and said imaging means preferably includes a laser, a flamp lamp, a light emitting diode or similar device.

In another embodiment of the invention, the remote-controlled, micro-scale device is not wireless, but rather, is connected to an electrical wire cable.

The present invention is made possible, in part, by the recent advent of enabling technology in the fields of microrobotics (see, for example, U.S. Pat. No. 5,610,488, inventor Miyazawa, which issued Mar. 11, 1997 and which is incorporated herein by reference) and microelectromechanical systems (MEMS) (see, for example, Motamedi et al., "Micro-opto-electro-mechanical devices and on-chip optical processing, *Opt. Eng.*, 36(5), 1282–97 (May 1997); Gonzalez et al., "Packaging Technology for Miniature IVD Instrumentation," Medical *Device & Diagnostic Industry*, 70–75 (April 1998); Motamedi et al., "Miniaturized micro-optical scanners," *Optical Engineering*, 33(11):3616–23 (November 1994); Lang, "Silicon microstructuring technology," *Material Science and Engineering*, R17, 1–55 (1996); and "A guitar the size of a cell," *New York Times*, Page C4 (Jul. 29, 1997), all of which are incorporated herein by reference).

Additional objects, as well as features, aspects and advantages of the present invention, will be set forth, in part, in the description which follows and, in part, will be obvious from the description or may be learned by practice of the invention. In the description, reference is made to the accompanying drawings which form a part thereof and in which is shown by way of illustration specific embodiments for practicing the invention. These embodiments will be described in sufficient detail to enable those skilled in the art to practice the invention, and it is to be understood that other embodiments may be utilized and that structural changes may be made without departing from the scope of the invention. The following detailed description is, therefore, not to be taken in a limiting sense, and the scope of the present invention is best defined by the appended claims.

BRIEF DESCRIPTION OF THE DRAWINGS

The accompanying drawings, which are hereby incorporated into and constitute a part of this specification, illustrate preferred embodiments of the invention and, together with the description, serve to explain the principles of the invention. In the drawings wherein like reference numerals represent like parts.

DETAILED DESCRIPTION OF PREFERRED EMBODIMENTS

The present invention is directed to a remote-controllable, micro-scale device which can be introduced into an animal (e.g., human) body by a minimally invasive procedure (e.g., by insertion through a natural body opening, such as the mouth, or by injection into the blood stream) and which can be used to travel to a variety of sites inside the body, such as the stomach, gallbladder, intestines, colon, rectum, prostate, kidney, liver, brain, and blood vessels. As will hereinafter be seen, according to one embodiment of the invention, the remote-controllable, micro-scale device is wireless and has complete freedom to move about inside a patient. In another embodiment, the remote-controllable, micro-scale device is connected by a wire cable to a computer system located externally relative to the patient's body. In any event, once at any of the aforementioned locations in a patient's body, the device can be used to detect the presence of abnormalities or disease states (e.g., by measuring the spectra of light emitted from an irradiated region), which information can be transmitted from the device to an outside operator for analysis. The operator can then instruct the device to render appropriate treatment, such as the ablation of tumors or blockages, the welding of ruptures, or the like.

Figure 1:
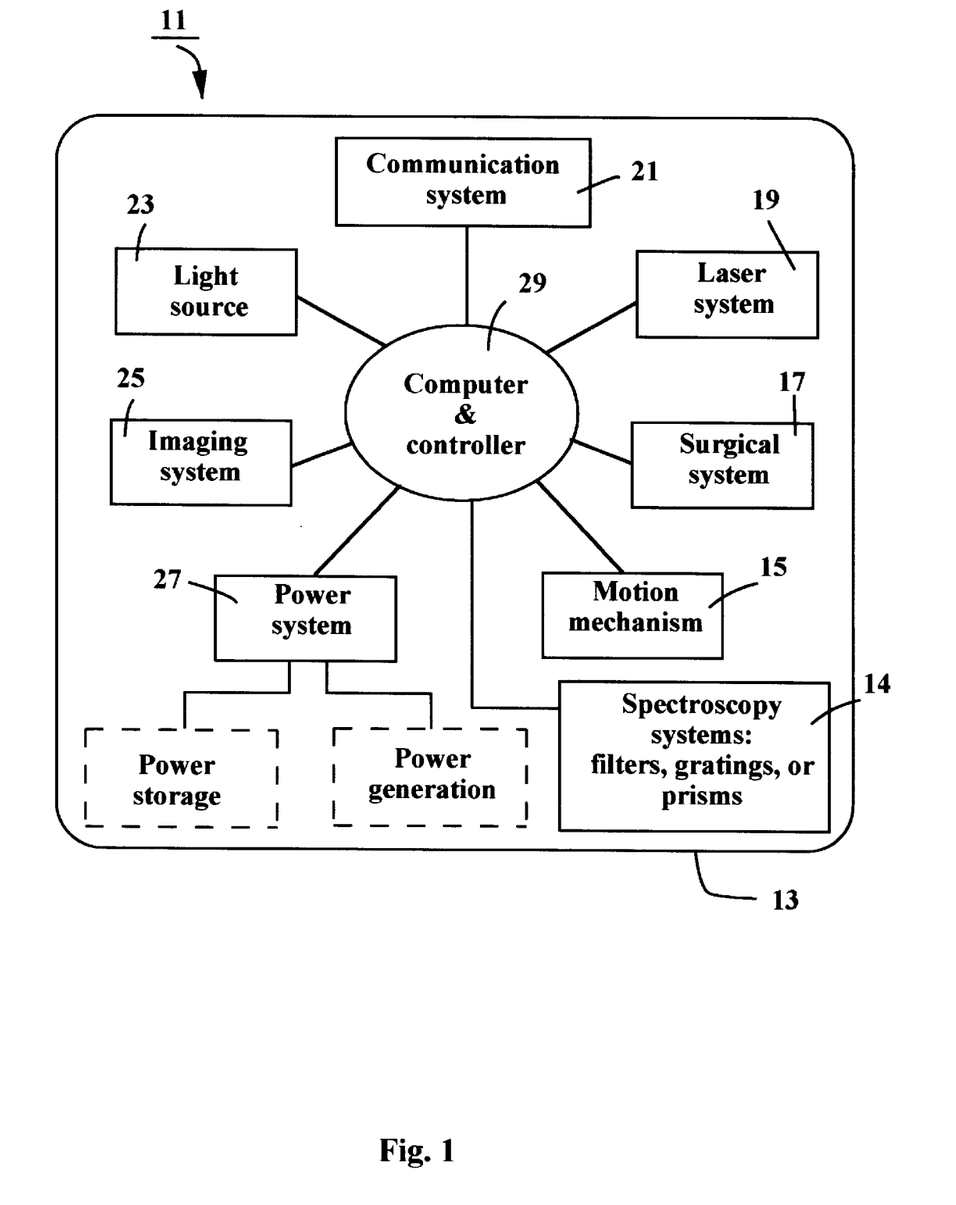
FIG. 1 is a block diagram of a first embodiment of a remote-controllable, micro-scale device adapted for use inside a patient's body, the remote-controlled, micro-scale device being constructed according to the teachings of the present invention.

Referring now to FIG. 1, there is shown a block diagram of a first embodiment of a remote-controllable, micro-scale device constructed according to the teachings of the present invention, the remote-controllable, micro-scale device being represented generally by reference numeral 11.

Device 11, which is a wireless, remote-controllable, micro-scale device, includes a transport capsule 13, capsule 13 being used to house some or all of the other components of device 11. Preferably, transport capsule 13 is made of a smooth and non-corrosive material, such as teflon, stainless steel, silicon or gold. The particular type of material of which capsule 13 is made is preferably selected to be most suitable depending upon whether device 11 is intended to take a gastrointestinal route through a patient (typically initiated by swallowing) or a blood circulatory route through a patient (typically initiated by injection into the blood stream). It can also be launched from an endoscope. Where device 11 is intended for gastrointestinal use, it preferably has a shape similar to a common medicinal tablet or capsule with a length of up to 20 mm and a radius of up to 2 mm. Where device 11 is intended for blood stream use (by injection through a large diameter needle or hollow tube), it preferably has dimensions smaller than 1 mm.

Device 11 also includes a spectroscopic system 14 (comprising, for example, transmission-type and/or reflection-type gratings and filters), a motion mechanism 15, a surgical system 17, a laser system 19, a communications system 21, a light source 23, an imaging system 25 and a power system 27, all of which are coupled to a microcomputer and controller 29.

Figure 2:
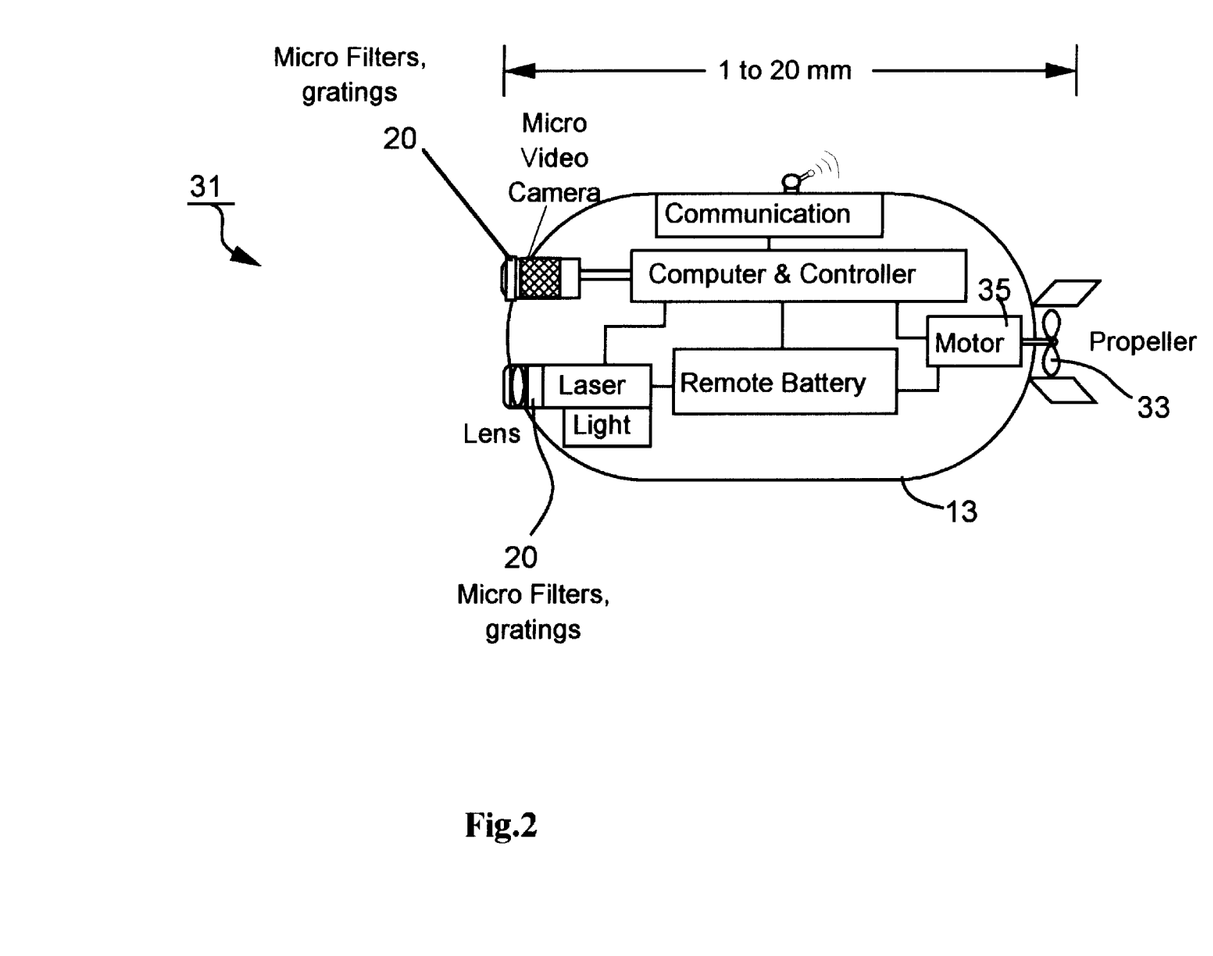
FIG. 2 is a schematic diagram of a first implementation of the remote-controllable, microscale device of FIG. 1, wherein the motion mechanism comprises a propeller.

Referring now to FIG. 2, there is shown a first implementation 31 of the remote-controllable, micro-scale device of FIG. 1. As can be seen, the motion mechanism of implementation 31 comprises a mechanical propeller 33. Where the device is intended for use in the blood stream, propeller 33 may be driven by an electric motor 35. Where the device is intended for use in the gastrointestinal system, propeller 33 may be turned by a build in gas flow.

Figure 3:
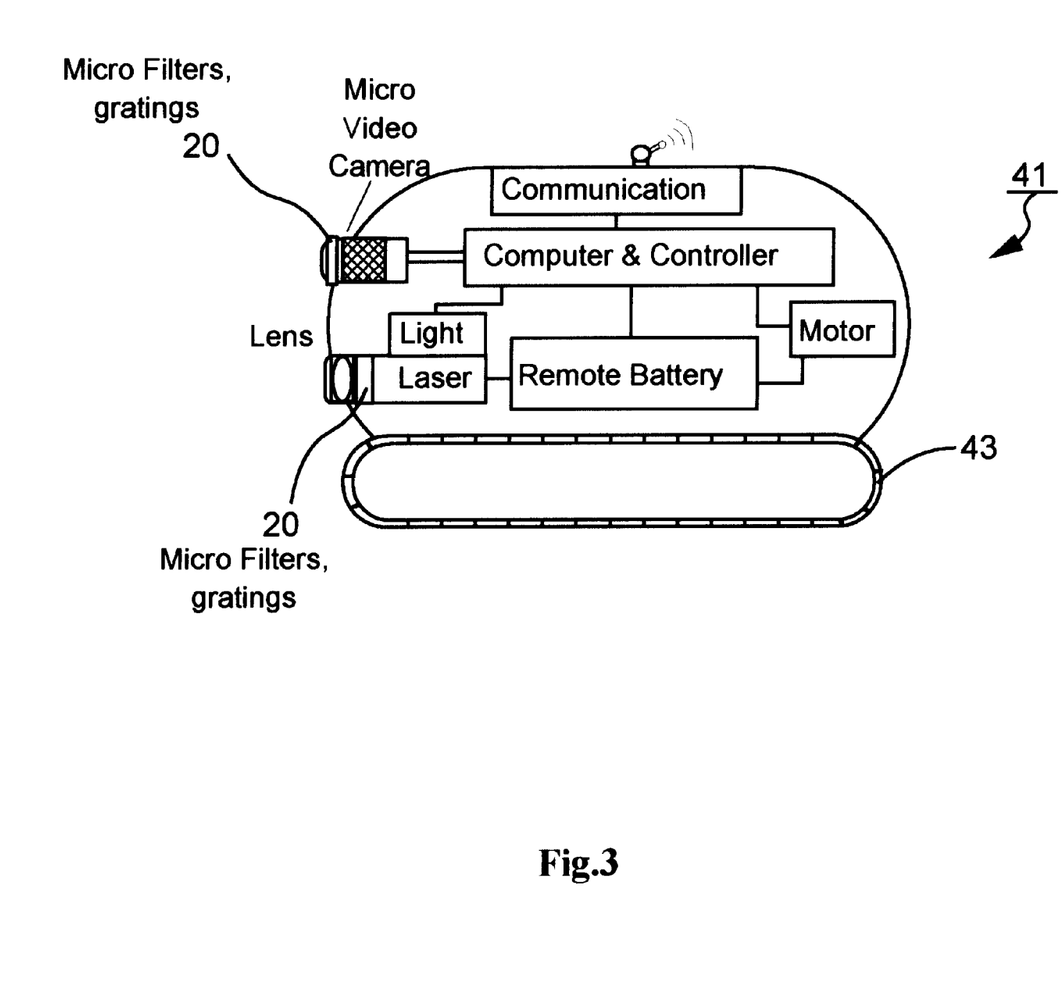
FIG. 3 is a schematic diagram of a second implementation of the remote-controllable, micro-scale device of FIG. 1, wherein the motion mechanism comprises micro tractor treads.

A second implementation 41 of the remote-controllable, micro-scale device of FIG. 1 is shown schematically in FIG. 3. In said implementation, the motion mechanism comprises micro tractor treads 43 for enabling the device to move on the inner surfaces of an organ. The device can be used to detect tissue properties using spectroscopy.

Figure 4A:
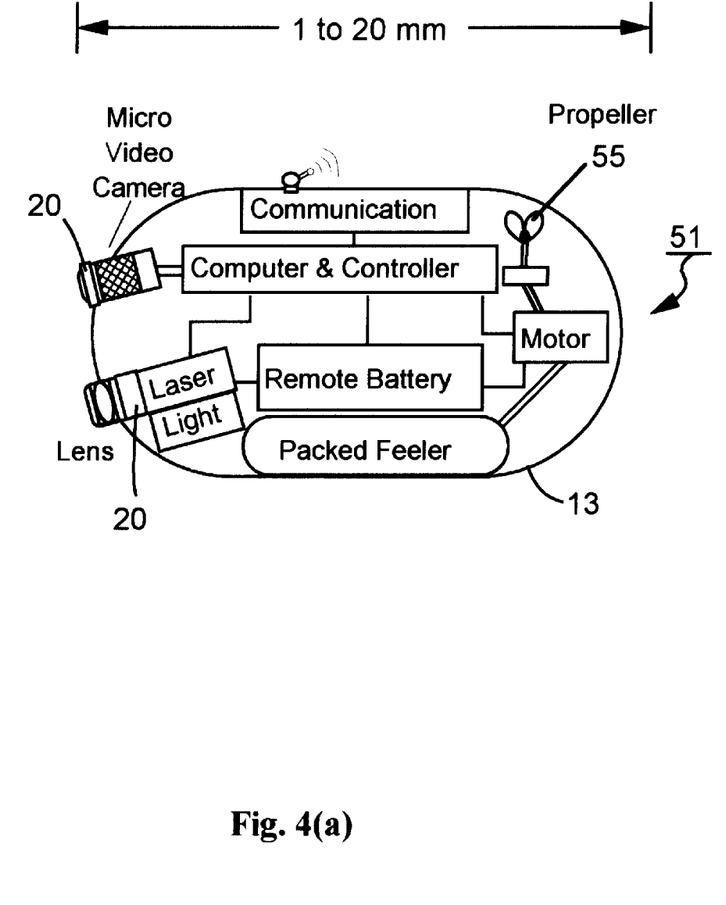
FIGS. 4(a) and 4(b) are schematic diagrams of a third implementation of the remote-controllable, micro-scale device of FIG. 1 shown before and after deployment of a motion mechanism comprising a propeller and a snail-type feeler.
Figure 4B:
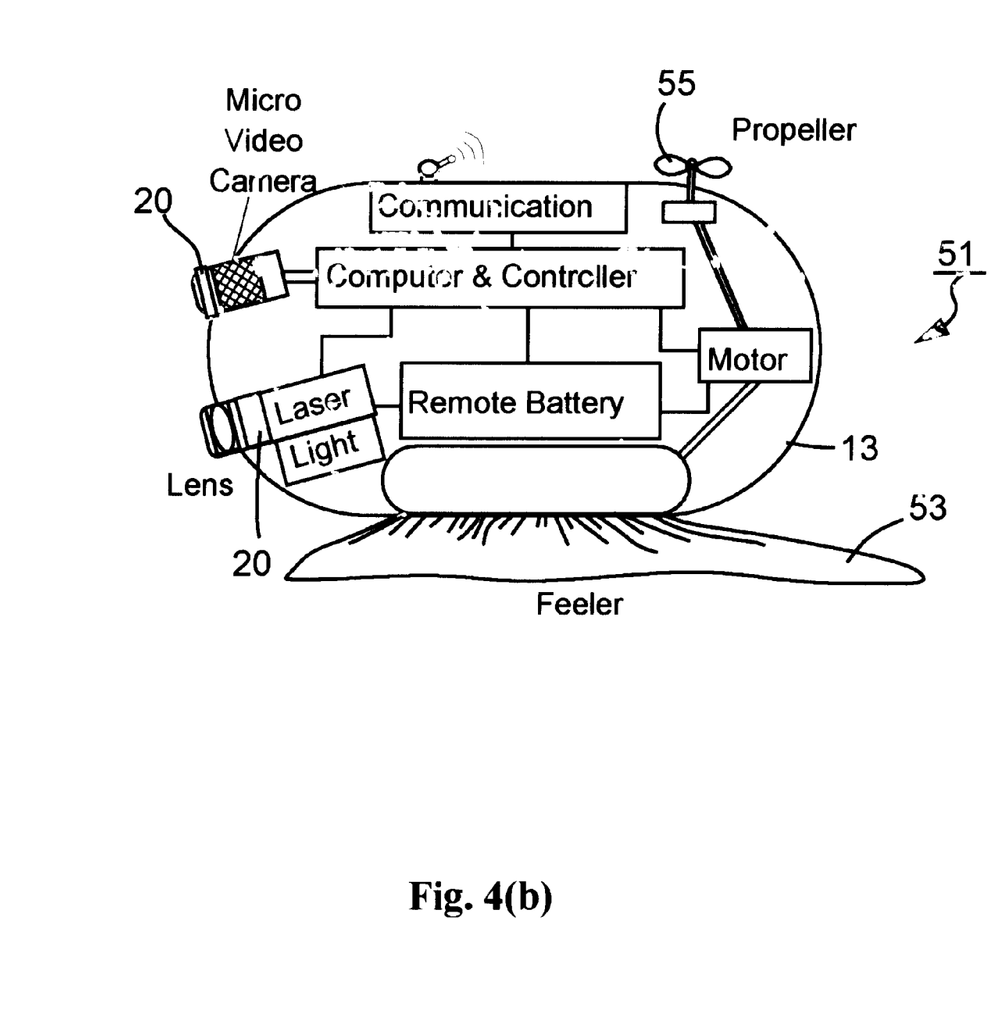

A third implementation 51 of the remote-controllable, micro-scale device of FIG. 1 is shown schematically in FIGS. 4(a) and 4(b). In said implementation, the motion mechanism comprises a suction-type conveyor belt 53 for enabling the device to move along the surfaces of an internal organ in a manner akin to the way a snail feeler operates. Preferably, the conveyor belt 53 is retractable to a position inside capsule 13 and is deployed after the device has been swallowed. As can be seen, the motion mechanism of implementation 51 also comprises a helicopter-type propeller 55, propeller 55 preferably being retractable to a position inside capsule 13 for deployment after the device has been swallowed.

Figure 5:
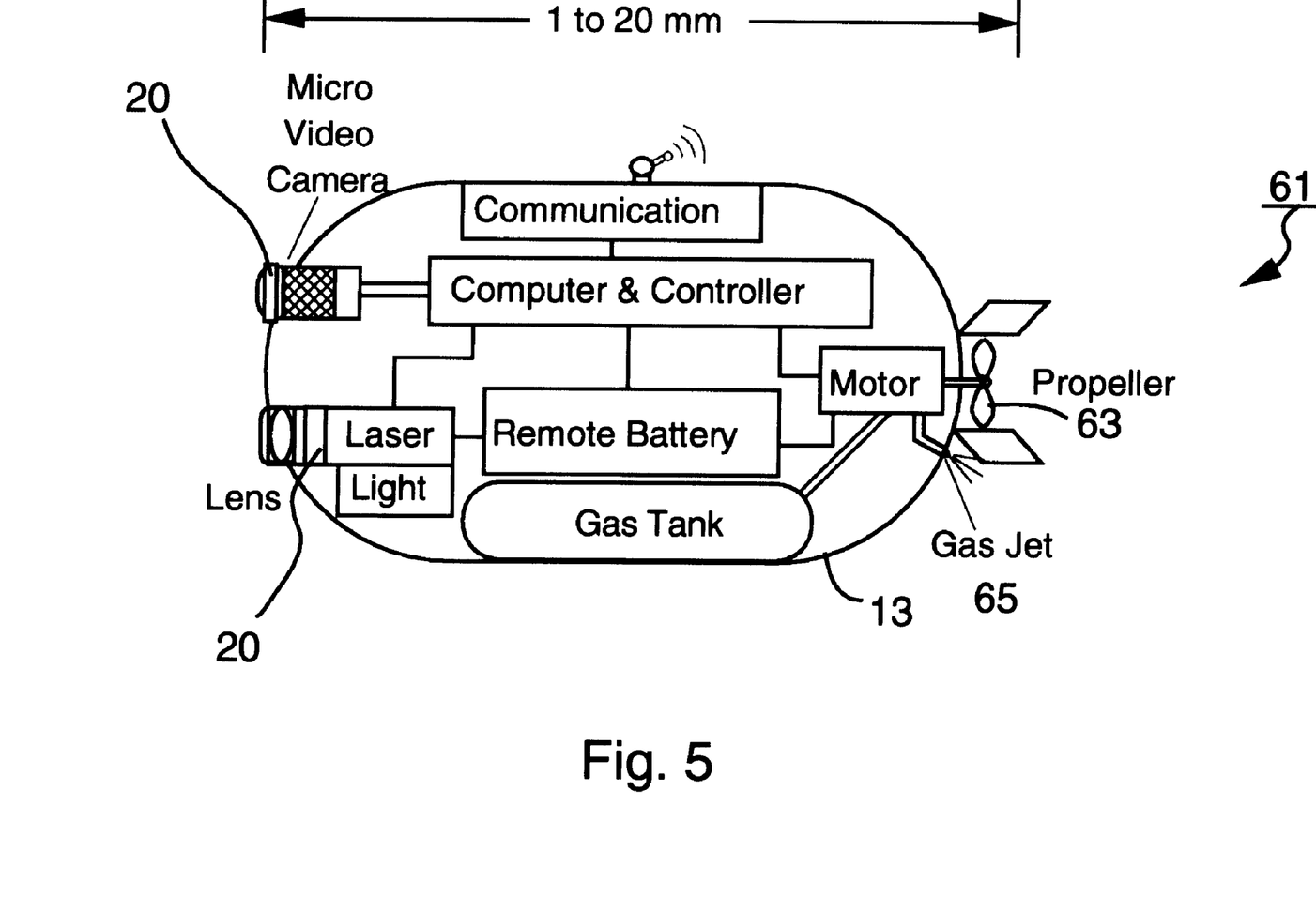
FIG. 5 is a schematic diagram of a fourth implementation of the remote-controllable, micro-scale device of FIG. 1, wherein the motion mechanism comprises a propeller in combination with a gas jet.

A fourth implementation 61 of the remote-controllable, micro-scale device of FIG. 1 is shown schematically in FIG. 5. In said implementation, the motion mechanism comprises a propeller 63 and a gas jet 65 for rocketing the device forward and to the sides.

Other types of motion mechanisms which may be usable in the remote-controllable, micro-scale device of FIG. 1 include means for generating snake-type motion, such as a multiple wheel system, and electromagnetic systems, such as a metal sensor in the device controlled by an external magnet.

The foregoing devices can measure local tissue properties in situ using spectroscopic features from fluorescence and Raman bands.

Referring back to FIG. 1, the power system for device 11 preferably is provided by a small seed internal battery and/or an external power source. An example of a micro-scale battery which may be suitable for use in device 11 is an advanced lightweight alkaline battery developed by United Technology Corp., said battery having a gold-plate magnesium co- or counterflow bipolar plate, a graphite electrolyte reservoir plate and a 50 $\mu$m matrix, with a total active component weight of about 0.16 gm/cm$^2$. The aforementioned battery is capable of delivering 9A/cm$^2$ at 0.72 V or 39 W/gm continuous power. A micro-scale battery of the foregoing type may be used to supply the necessary power for the internal computer operation and controllers of device 11. Other internally-disposed power sources include standard high efficiency micro-batteries to generate electric currents and high density chemical batteries wherein two or more chemicals are mixed to release a significant amount of energy as a source to generate electric energy (this energy being an ideal source for high power lasers to conduct surgical operations). Still another possible power source is x-rays, translucent through the human body, to absorbers on the device—the absorbed energy is then converted by the device to power to drive the device.

Figure 6:
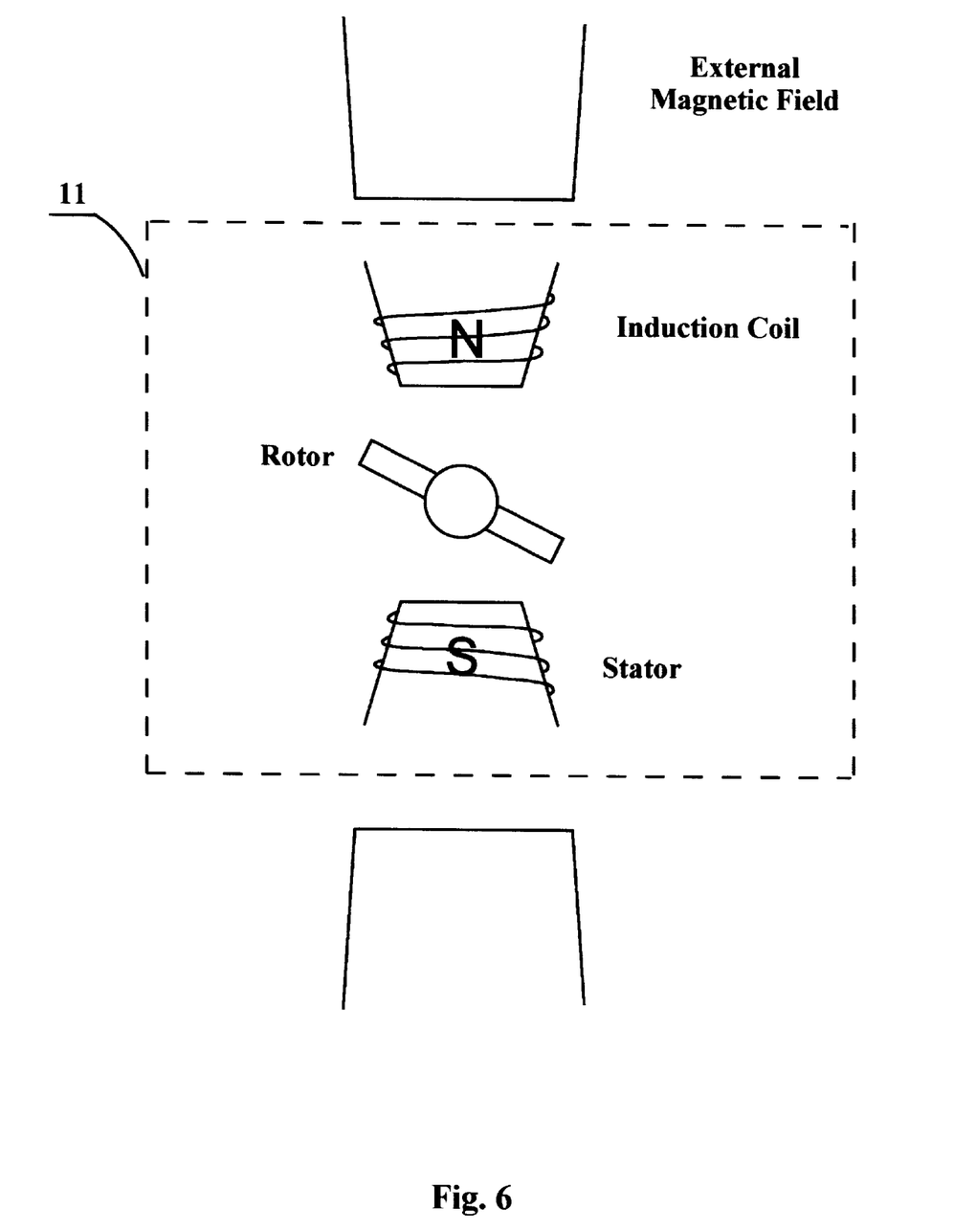
FIG. 6 is a schematic diagram of a modified induction motor based electric generator for use in the device of FIG. 1.

However, due to the finite size of the device, the major power requirement for motion, communications and laser operation is typically delivered by external pumped power sources. One example of an external pumped power source is a remote induction generator. As seen in FIG. 6, a modified induction motor-based electric generator can be disposed inside the device, with an external time-varied powered magnetic field used to rotate a rotor inside the device, the rotated rotor then being used to generate electric current. Another external pumped power source is a remote microwave delivery system comprising EM antennae or receivers with high absorption coefficient and resonance geometrical arrangement built inside the device to collect external microwave energy at a designated wavelength. Still another external pumped power source is a remote ultrasound delivery system comprising piezoelectric receivers built inside the device to collect external ultrasonic energy to power the device and to charge-up an internal battery.

The communications system of device 11 preferably comprises one or more microscopic resonating-beams as small as 30 $\mu$m long and 8 $\mu$m wide that are anchored at each end to a silicon chip, with the respective midsections of the beams suspended about 0.1 $\mu$m above the chip surface. When the requisite radio-frequency signal voltage is applied to an electrode under the beams, the resulting electrostatic force makes the hanging section of the beams vibrate up and down at frequencies of nearly 15 MHz, enabling two-way radio signals to be radiated to and from the device. As can readily be appreciated, by adding a signal processor to the above-described silicon chip, one can construct two-way radios, telephones and modems as small and as inexpensive as can be imagined.

The imaging system of device 11 preferably comprises a micro-video CCD with LED light sources built on small scale computer chips. Micro flash lamps can be used to illuminate areas to be imaged. The LED light sources are preferably three color LED diodes based on MBES technology to generate quantum well emissions. The data collected from the CCD is digitized and transmitted by radio waves to an external computer system to be displayed, stored and analyzed.

A spectroscopic imaging system in device 11 is incorporated into the device and is connected to the CCD image system (or photodiodes, such as avalanche diodes) to improve the sensitivity of the disease diagnosis. Micro scale narrow band filters, color filter system and/or gratings can be added to the illumination source from laser, flash lamp, LED and the collected signal of the CCD camera, photodiode, avalanche photodiodes or PMT to obtain the spectroscopic information on the disease area. Wide-band dielectric filters on the device can be used to separate various colors emitted or absorbed. The filters may be rotated on a MEMS rotation wheels to select different wavelengths to measure light intensities for processing and image analysis to diagnosis.

Figure 7A:
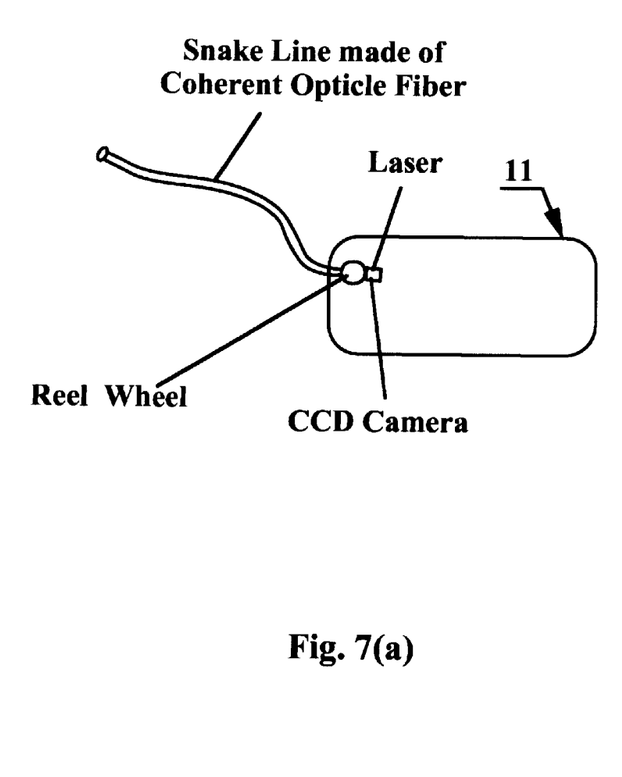
FIGS. 7(a) and 7(b) are schematic diagrams of two different embodiments of a remote micro-snake-like probe for use in the device of FIG. 1.
Figure 7B:
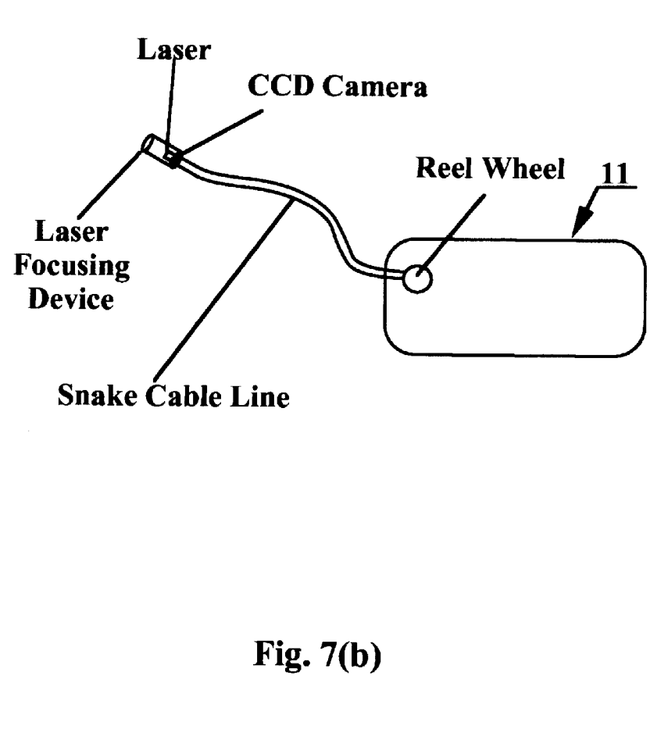

To detect areas remote from the device, such as a stone in a gallbladder, a coherent fiber may be installed in the device and attached to the CCD camera to form a snake-like probe less than 1 mm in diameter, as shown in FIG. 7(*a*), or the CCD camera and the laser may be installed on the tip of a snake-like cable, as shown in FIG. 7(*b*). The fiber is reeled out from the transport capsule like a fishing rod. These snake-like probes can wiggle into a small organ, such as the gallbladder, while the rest of the device holds in position more remotely. The spectroscopic and visual information can be transmitted to an operator outside the body for diagnosis and instructions for treatment.

The light source for device 11 is preferably one or more micro-scale, color light-emitting-diodes (LEDs), lasers based on quantum wells or a photographic flash lamp.

A micro-scale, solid-state, semiconductor diode laser system or a flash lamp may be used either as an illumination source or as a surgical source to ablate tissue or to weld tissues together. This laser is controlled by a computer and/or by a remote system operated by an operator or medical personnel. If an abnormal tissue or cancer has been clearly identified with the spectroscopic diagnostic system, a surgeon can control the surgical laser to remove those abnormal tissues with the aid of the video imaging system. The power flux on a spot near the device will be on the order of 100 W/cm$^2$ on an area of 10 $\mu$m$^2$. Using picosecond lasers, the power flux density can be greater than the value of $10^8$ W/cm$^2$. Using a photographic flash lamp, the power flux density on a spot can be on the order of Kw/cm$^2$. Optical filters will be used to select the different wavelengths to excite and measure the emission features.

Figure 8:
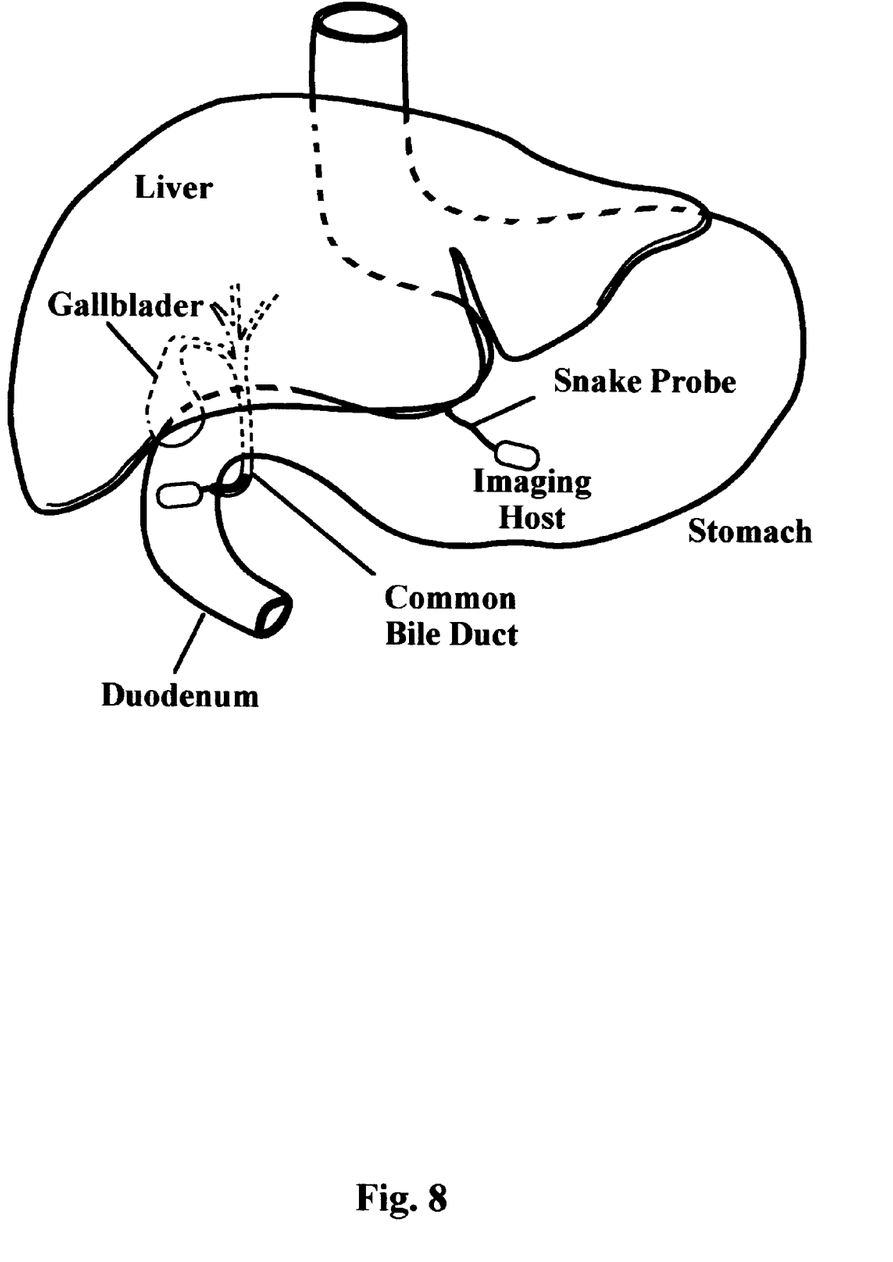
FIG. 8 is a schematic diagram of the device of FIG. 7(b) being used to take the spectra of a tissue for cancer diagnosis and to remove a stone from a gallbladder.

For a remote area laser surgical procedure, such as the removal of a stone from a gallbladder, the laser head can be mounted on a snake like cable, as in FIG. 8. The laser pulse can be directly impinged onto the target area to minimize the power loss with the greatest position accuracy.

Figure 9:
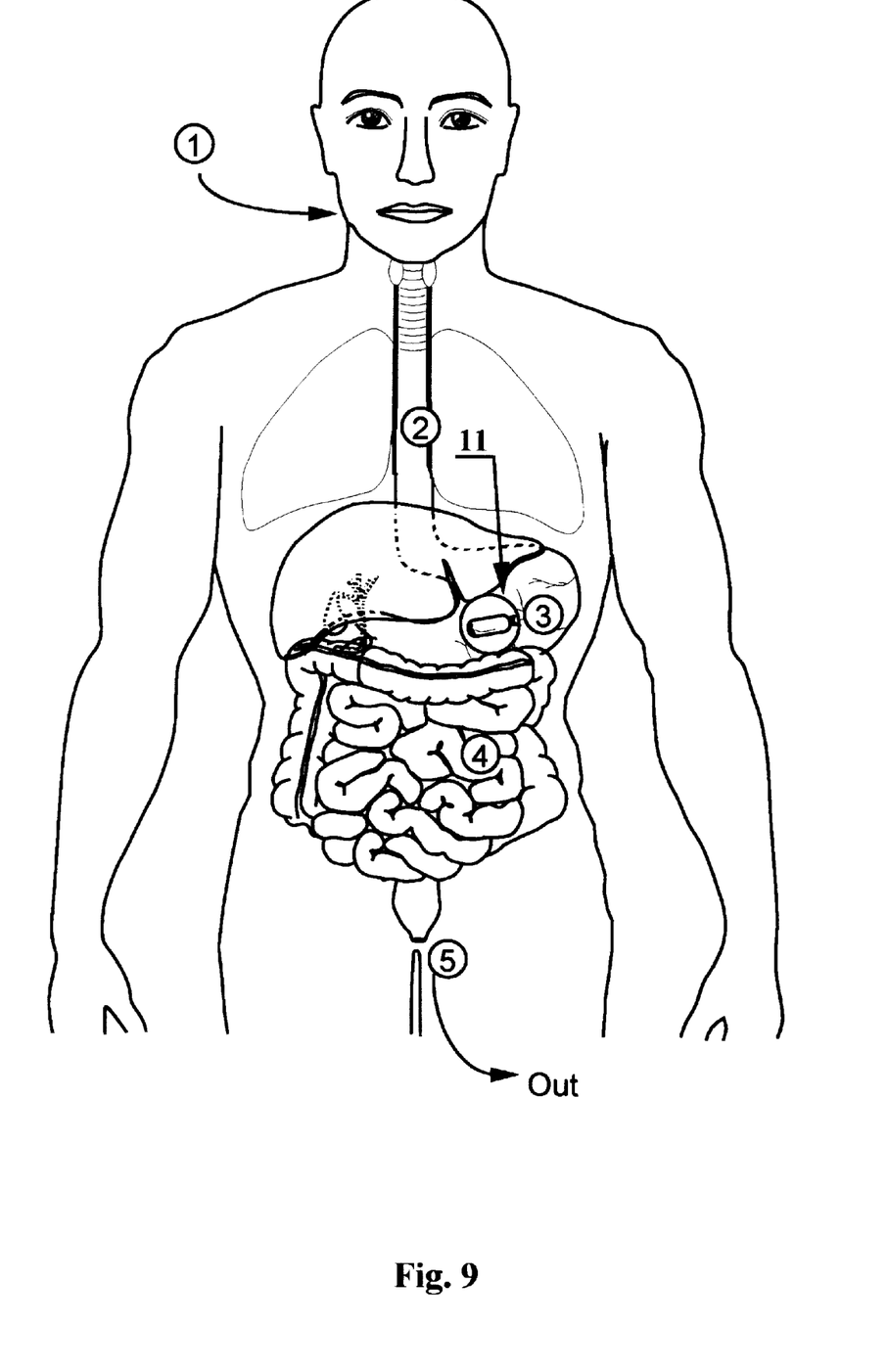
FIG. 9. is a schematic diagram of the path that the device of FIG. 1 takes after having been ingested orally.
Figure 10:
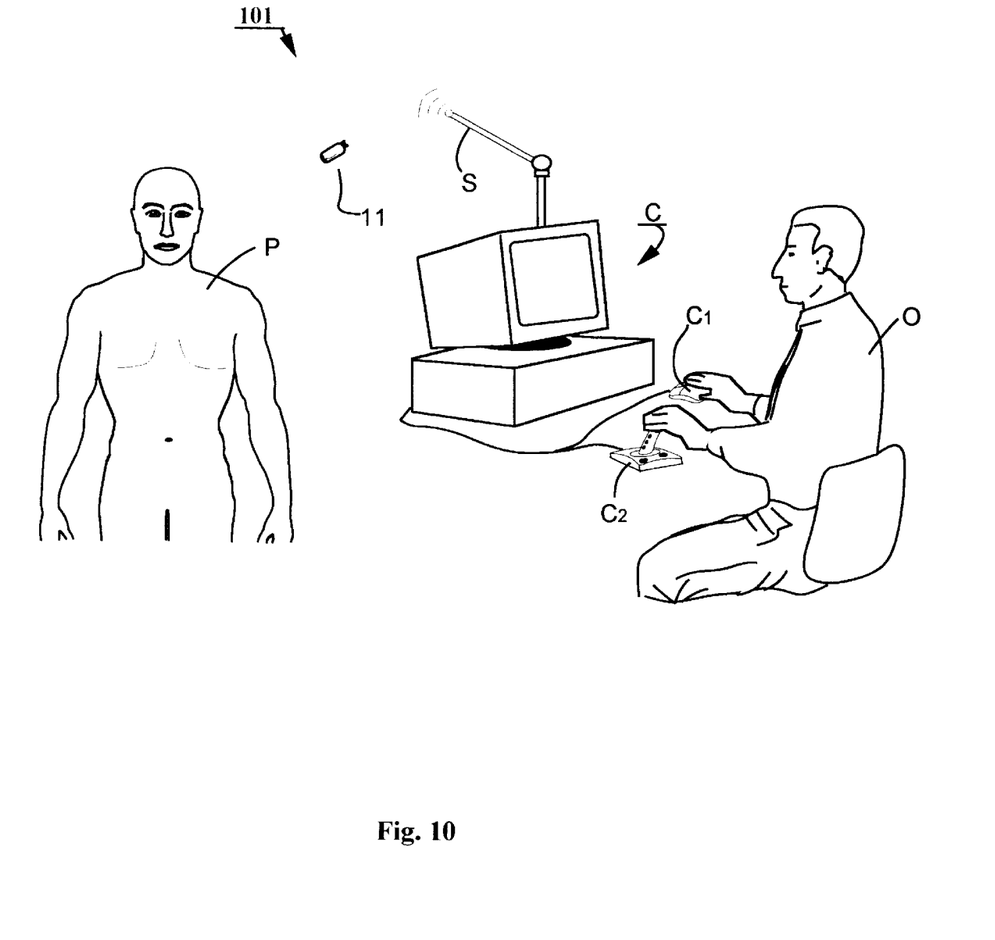
FIG. 10 is a schematic diagram of a system comprising the device of FIG. 1 used by an operator to examine a patient.

FIG. 9 illustrates schematically the path that device 11 takes after having been ingested orally (1-mouth, 2-esophagus, 3-stomach, 4-intestines and colon, and 5-out through rectum). FIG. 10 illustrates schematically a system 101, system 101 comprising device 11 and a computer system C, computer system C including a communications system S and controllers $C_1$ and $C_2$. System 101 is shown being used by an operator O to examine a patient P.

Figure 11A:
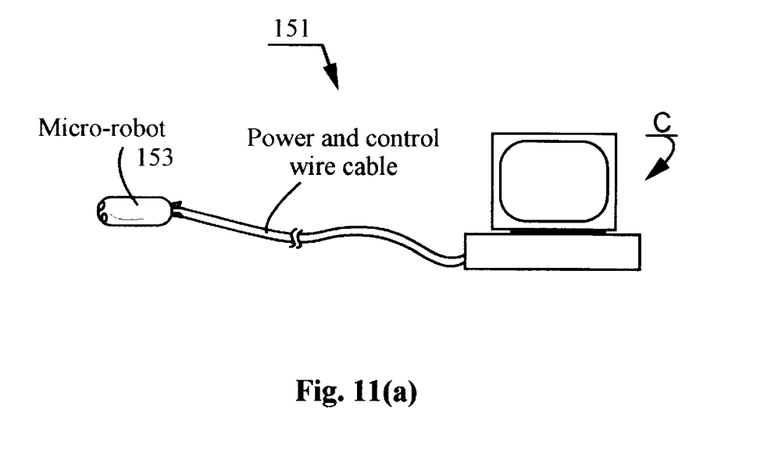
FIG. 11(a) is a schematic diagram of a system comprising a second embodiment of a remote-controllable, micro-scale device adapted for use inside a patient's body, said remote-controllable, micro-scale device being powered, operated and controlled through a wire cable.

Referring now to FIG. 11(a), there is shown a schematic diagram of another system comprising a remote-controllable, micro-scale device adapted for use inside a patient's body, said system being represented generally by reference numeral 151.

Figure 11B:
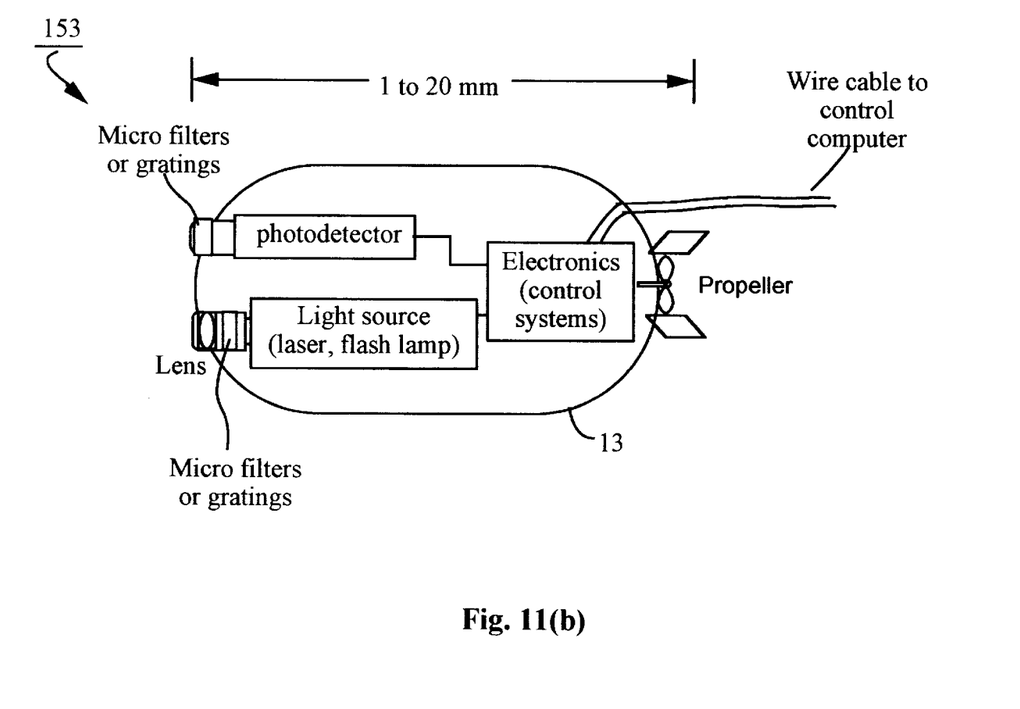
FIG. 11(b) is an enlarged schematic diagram of the remote-controllable, micro-scale device shown in FIG. 11(a).

System 151 comprises a remote-controllable, micro-scale device 153, device 153 being shown in greater detail in FIG. 11(b). Like device 11, device 153 comprises light sources, optical spectroscopic units of narrow band filters or micro gratings and a photo detector or a photomultiplier. Device 153 differs most significantly from device 11 in that device 153 is not wireless, but rather, is connected to an external computer system C' (the controllers of computer system C' not being shown in FIG. 11(a) but being the same as that of computer system C) via a wire cable. The operation commands and electrical power are delivered to device 153 through the wire cable from control computer system C'. The signals obtained by device 153 are sent through the wire cable to control computer system C' for analysis. The operation of device 153 may be controlled using a wire cable in an endoscope.

The embodiments of the present invention recited herein are intended to be merely exemplary and those skilled in the art will be able to make numerous variations and modifications to it without departing from the spirit of the present invention. All such variations and modifications are intended to be within the scope of the present invention as defined by the claims appended hereto.

What is claimed is:

1. A wireless, remote-controllable, micro-scale device adapted for use inside a patient's body, said wireless, remote-controllable, micro-scale device comprising:
   (a) a transport capsule;
   (b) means for moving said transport capsule inside a patient's body;
   (c) imaging means, on board said transport capsule, for collecting image information on the appearance of the inside of the patient's body;
   (d) examining means, on board said transport capsule, for collecting spectroscopic information regarding the presence of abnormal biological materials inside the patient's body; and
   (e) communication means, on board said transport capsule, for transmitting the information collected by said imaging means and said examining means to a location outside the patient's body.

2. The wireless, remote-controllable, micro-scale device as claimed in claim 1 wherein said moving means comprises at least one of an air propeller, a liquid propeller, a gas assisted propeller, snail motion means, snake motion means, micro tractor treads, and multiple wheels.

3. The wireless, remote-controllable, micro-scale device as claimed in claim 1 wherein said transport capsule has a length of about 20 mm.

4. The wireless, remote-controllable, micro-scale device as claimed in claim 1 wherein said transport capsule has a length of less than about 20 mm.

5. The wireless, remote-controllable, micro-scale device as claimed in claim 1 wherein said examining means comprises a light source for irradiating an area of the patient's body and means for detecting light from the irradiated area at one or more wavelengths.

6. The wireless, remote-controllable, micro-scale device as claimed in claim 5 wherein said light source is selected from the group comprising a semiconductor laser with/without harmonic generator, an LED, and a flash lamp with wavelength selection filters covering from 250 nm to 1400 nm.

7. The wireless, remote-controllable, micro-scale device as claimed in claim 5 wherein said detecting means comprises at least one of a CCD system, a photo-multiplier tube and a photo avalanche diode using a small scale multiple color selector.

8. The wireless, remote-controllable, micro-scale device as claimed in claim 7 wherein said small scale multiple color selector comprises at least one of a grating, a prism, a wide band filter set and one or more narrow band filter sets.

9. The wireless, remote-controllable, micro-scale device as claimed in claim 1 further comprising means on board said transport capsule for treating the patient's body.

10. The wireless, remote-controllable, micro-scale device as claimed in claim 9 wherein said treatment means comprises a laser for ablating and/or welding tissue.

11. The wireless, remote-controllable, micro-scale device as claimed in claim 10 wherein said laser is mounted on a cable extending away from the transport capsule.

12. The wireless, remote-controllable, micro-scale device as claimed in claim 1 wherein said moving means comprises a movable member for providing said transport capsule with motility and a power source for moving said movable member.

13. The wireless, remote-controllable, micro-scale device as claimed in claim 12 wherein said power source is a battery.

14. The wireless, remote-controllable, micro-scale device as claimed in claim 13 wherein said battery is at least one of a standard high efficiency micro-battery and a high density chemical battery.

15. The wireless, remote-controllable, micro-scale device as claimed in claim 1 wherein said moving means comprises a movable member for providing said transport capsule with motility and means for powering the movement of said movable member, said powering means being energizable by an external source.

16. A system for use in internally examining a patient, said system comprising:
   (a) a computer, said computer comprising means for receiving wireless signals; and
   (b) the wireless, remote-controllable, micro-scale device as claimed in claim 1.

17. A method of examining a patient comprising the steps of:
   (a) providing the wireless, remote-controllable, micro-scale device of claim 1;
   (b) introducing the wireless, remote-controllable, micro-scale device into the patient; and
   (c) transmitting the image and/or examination information collected by said collecting means to a receiver located outside of the patient's body.

18. The method as claimed in claim 17 wherein said moving means of said wireless, remote-controllable, micro-scale device comprises at least one of an air propeller, a liquid propeller, a gas assisted propeller, snail motion means, snake motion means, micro tractor treads and multiple wheels and wherein said device further comprises means for treating the patient.

19. The method as claimed in claim 17 wherein said wireless, micro-scale device is introduced into the patient orally.

20. The method as claimed in claim 17 wherein said wireless, micro-scale device is introduced into the patient intravenously.

21. The wireless, remote-controllable, micro-scale device
   (a) as claimed in claim 1 wherein said transport capsule is 0.1 mm to 20 mm in length.

22. The wireless, remote-controllable, micro-scale device as claimed in claim 21 wherein said examining means comprises a light source, the light source being selected from the group comprising semiconductor lasers, flash lamps, and LED's.

23. The wireless, remote-controllable micro-scale device as claimed in claim 22 wherein said examining means also comprises a photodetector, the photodetector being selected from the group comprising photo diodes, avalanche photodiode, and photomultiplier tube (PMT).

24. The wireless, remote-controllable micro-scale device as claimed in claim 23 wherein said examining means further comprises changeable optical filters or transmission gratings.

25. The wireless, remote-controllable, micro-scale device as claimed in claim 24 wherein the device diagnoses diseases in vivo of stomach, GI track, prostate, blood vessels, heart, GYN track, and ducts of breast.

26. The wireless remote-controllable, micro-scale device as claimed in claim 25 wherein optical filters are moved into position to select wavelengths using microelectromechanical gears.

27. A wireless, remote-controllable, micro-scale device adapted for use inside a patient's body, said wireless, remote-controllable, micro-scale device comprising:
   (a) a transport capsule;
   (b) means for moving said transport capsule inside a patient's body;
   (c) imaging meas, on board said transport capsule, for collecting image information on the appearance of the inside of the patient's body;
   (d) examining means, on board said transport capsule for collecting information regarding the presence of abnormal biological materials inside the patient's body wherein said examining means comprises a light source for irradiating an area of the patient's body and means for detecting light from the irradiated area at one or more wavelengths and wherein said examining means measures native fluorescence information from the irradiated area; and
   (e) communication means, on board said transport capsule, for transmitting the information collected by said imaging means and said examining means to a location outside the patient's body.

28. A wireless, remote-controllable, micro-scale device adapted for use inside a patient's body, said wireless, remote-controllable, micro-scale device comprising:
   (a) a transport capsule;
   (b) means for moving said transport capsule inside a patient's body;
   (c) imaging meas, on board said transport capsule, for collecting image information on the appearance of the inside of the patient's body;
   (d) examining means, on board said transport capsule, for collecting information regarding the presence of abnormal biological materials inside the patient's body wherein said examining means comprises a light source for irradiating an area of the patient's body and means for detecting light from the irradiated area at one or more wavelengths and wherein said examining means measures native Raman information from the irradiated area; and
   (e) communication means, on board said transport capsule, for transmitting the information collected by said imaging means and said examining means to a location outside the patient's body.

29. A system for use in internally examining a patient, said system comprising:
   (a) a computer;
   (b) a micro-scale device comprising
      (i) a transport capsule, said transport capsule being 0.1 mm to 20 mm in length;
      (ii) means for moving said transport capsule inside a patient's body;
      (iii) imaging means, on board said transport capsule, for collecting image information on the appearance of the inside of the patient's body;
      (iv) examining means, on board said transport capsule, for collecting spectroscopic information regarding the presence of abnormal biological materials inside the patient's body; and
   (c) a wire cable electrically connecting said micro-scale device to said computer.

30. The system as claimed in claim 29 wherein said micro-scale device further comprises means for moving said transport capsule inside a patient's body.

* * * * *